United States Patent [19]

Carter

[11] 4,240,878
[45] Dec. 23, 1980

[54] METHOD OF FORMING A PLATINUM LAYER ON TANTALUM

[75] Inventor: William W. Carter, Conesus, N.Y.
[73] Assignee: Sybron Corporation, Rochester, N.Y.
[21] Appl. No.: 90,630
[22] Filed: Nov. 2, 1979

Related U.S. Application Data

[63] Continuation-in-part of Ser. No. 923,814, Jul. 12, 1978, abandoned.

[51] Int. Cl.³ .............................................. G01R 31/12
[52] U.S. Cl. ................................. 204/1 T; 204/37 R; 204/290 F; 324/54
[58] Field of Search ................. 204/1 T, 37 R, 290 F; 324/54, 425

[56] References Cited

U.S. PATENT DOCUMENTS

| | | | |
|---|---|---|---|
| 2,497,090 | 2/1950 | Miller et al. | 204/37 R |
| 2,719,797 | 10/1955 | Rosenblatt et al. | 204/37 R |
| 2,847,372 | 8/1958 | Dijksterhuis | 204/37 R |
| 3,129,163 | 4/1964 | Stern et al. | 204/290 |
| 3,461,058 | 8/1969 | Haley et al. | 204/290 |
| 3,831,085 | 8/1974 | Kratavil | 324/54 |
| 3,858,114 | 12/1974 | Voellmin et al. | 324/54 |
| 3,863,146 | 1/1975 | Ehret | 324/54 |

OTHER PUBLICATIONS

Beckman Instruments Inc., Instruction Manual for Conductivity Bridge RC-16C, Part No. 015-10748184, 6/1976, Ceder Grove, N.J. 07009, p. 9.

*Primary Examiner*—Howard S. Williams
*Assistant Examiner*—William Leader
*Attorney, Agent, or Firm*—Theodore B. Roessel; Owen D. Marjama

[57] ABSTRACT

A method of platinizing and heat treating tantalum metal is described. The platinizing of tantalum is accomplished by placing a piece of conductive corrosion resistant metal and a tantalum workpiece as electrodes in a platinizing solution. The electrodes are connected to a source of DC power supply and when the current is passed, platinum black is deposited on the tantalum workpiece. The platinized tantalum workpiece is then placed in a furnace maintained at a temperature of about 1050° to 1150° C. for a time sufficient to diffuse the coated platinum into the surface of the tantalum core. The method of using the electrode for the detection of faults in a glass lined apparatus is also disclosed.

4 Claims, 1 Drawing Figure

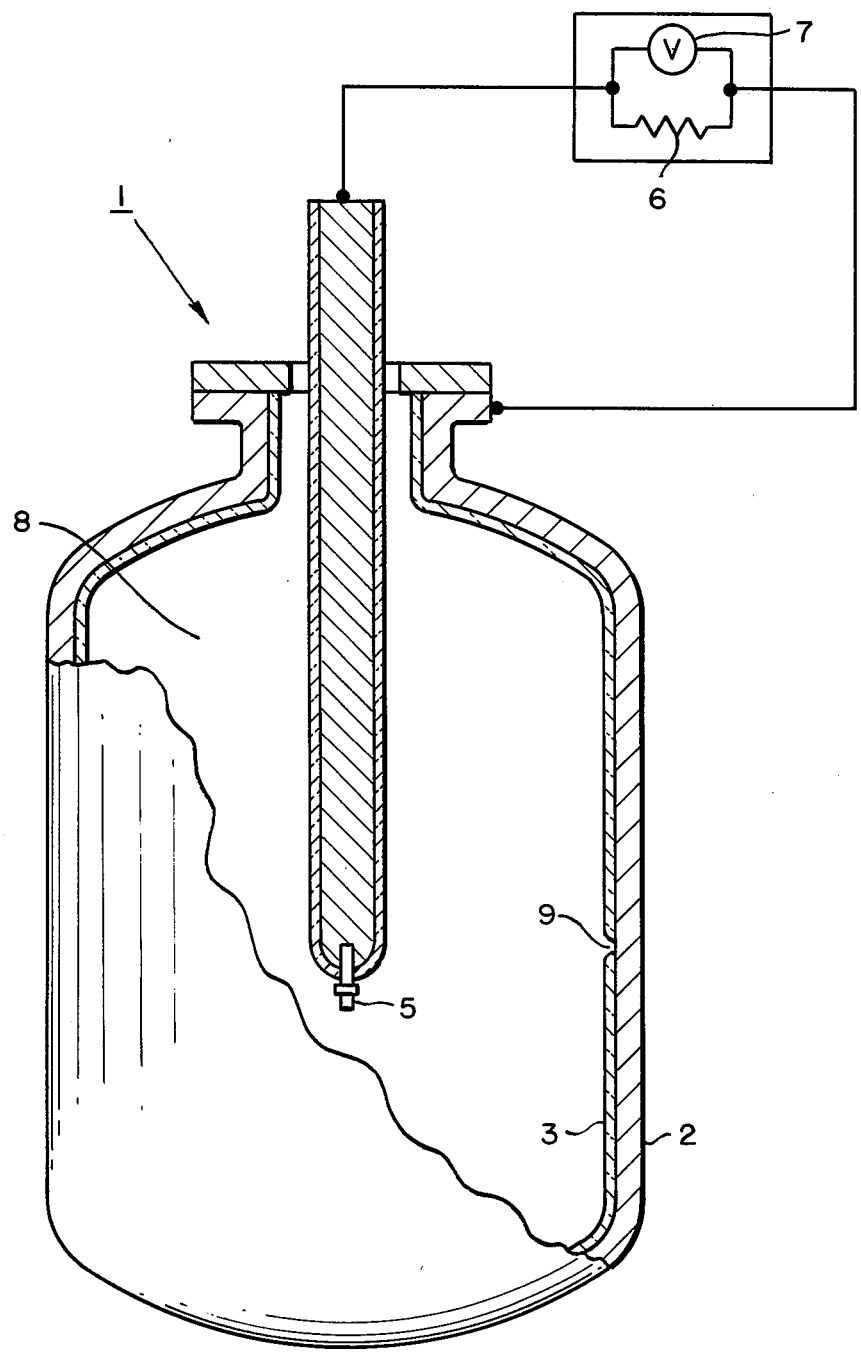

METHOD OF FORMING A PLATINUM LAYER ON TANTALUM

RELATED APPLICATIONS

This application is a continuation-in-part of Applicant's copending application Ser. No. 923,814, filed July 12, 1978, now abandoned.

BACKGROUND OF THE INVENTION

This invention relates to a method of platinizing and heat treating tantalum and more particularly tantalum plugs to be used as electrodes in the detection of faults in reaction vessel protective linings.

It is a common practice to use protective layers of glass enamel as an anti-corrosive lining on the inside of reaction vessels which contain corrosive liquids. In such vessels, a fault in the protective lining can result in serious corrosion of the vessel, and if such a fault remains undetected for some time, the vessel may become unusable and irreparable. In some cases, the contents of the vessel may even become contaminated. Thus, it can be seen that vessels of this type must be continuously monitored against damage to the protective lining.

U.S. Pat. No. 3,858,114, which is incorporated herein by reference, discloses a method for detecting faults in reaction vessel linings. The method described in this patent involves disposing a platinum electrode in a conductive medium in the vessel and measuring any current flowing from the electrode to the iron or steel wall of the reaction vessel. At locations where damage has occurred to the lining, the current flow increases accordingly. The intensity of the current delivered by the so formed Pt-Fe cell indicates the degree of damage to the protective layer. The platinum metal used as an electrode in U.S. Pat. No. 3,858,114 is very expensive. It would therefore be worthwhile, if possible, to plate a tantalum core with platinum and use it as an electrode. Such an electrode would have a platinum surface and tantalum core and would be less expensive than conventionally platinum plated electrodes. Tantalum has been chosen as a core material because it is corrosion resistant and should the platinum layer of the electrode break down, the tantalum will not adversely affect the contents of the vessel. It has been found in practice, however, that conventionally plated platinum layers on tantalum wear out rather quickly, particularly when the contents of the vessel contain an abrasive material such as slurry.

OBJECTS OF THE INVENTION

Accordingly, it is an object of this invention to provide an abrasion resistant platinum layer on the outer surface of a tantalum workpiece.

It is another object of this invention to provide a method of platinizing and heat treating a tantalum workpiece.

It is yet another object of this invention to provide an improved electrode for a reaction vessel fault finder of high precision.

It is a further object of this invention to provide a method of obtaining a thin stable layer of platinum on a tantalum workpiece.

It is yet another object of the invention to provide an inexpensive platinum electrode and method for detecting faults in a glass lined apparatus.

SUMMARY OF THE INVENTION

These objects and others are accomplished in accordance with the present invention by providing a novel method of platinizing and heat treating a tantalum workpiece. The surface of the workpiece is first cleaned and then connected to the negative lead of a source of DC supply. The positive lead of the DC supply is then connected to a piece of corrosion resistant conductive metal, such as platinum, and both metals immersed in a platinizing solution. A current is then passed through the solution and platinum black is deposited on the tantalum workpiece. The tantalum workpiece is then removed from the platinizing solution and heated to a temperature of about 1050–1150° C. in a vacuum furnace, or furnace containing an inert atmosphere, for a time sufficient to diffuse the platinum into the surface of the tantalum. This results in the formation of a tantalum workpiece which contains a stable outer layer of platinum diffused in the surface of the tantalum. This workpiece has utility as a preferred use as an electrode which is used to detect faults in a glass lined apparatus. This process may also be utilized to manufacture platinum coated parts such as electrodes, electrical probes, and repair plugs for glass lined vessels.

It should be understood that tantalum and tantalum base alloys which may be platinized and heat treated are included within the scope of this invention. For example, tantalum alloyed with tungsten comprises a suitable alloy which may be used in place of tantalum in the process of the present invention.

DETAILED DESCRIPTION OF THE INVENTION

One preferred embodiment of utilizing the platinum coated electrode of the present invention is described with reference to the following drawing. Referring to the sole FIGURE of the drawings, the apparatus 1 shown schematically in cross section has a steel wall 2, the inside surface of which is coated with an glass layer 3. A platinum coated electrode 5 which is made by the method of the present invention, and which is electrically insulated from the apparatus, is disposed inside the apparatus. The platinum electrode is connected to the wall 2 of the apparatus via a 100 ohm measuring resistance 6 which lies outside the apparatus. A millivoltmeter and/or indicator device 7 is connected in parallel with the resistance.

When a fault occurs in the glass layer and when there is an electrically conductive medium 8 in the apparatus, a Pt-Fe cell is formed between the platinum electrode 5 and the exposed steel surface 9. The current delivered by this cell then flows through the measuring resistance 6. This current, which is measured using the millivoltmeter 7 by measurement of the voltage drop across the measuring resistance 6, is an indication of the rate at which iron is going into solution and thus the extent of the damage to the glass layer.

Within this disclosure, the terms platinum plated and platinized are specifically distinguished from each other. Platinum plating is carried out by conventional methods. A well cleaned tantalum workpiece is fastened in a chuck which is electrically charged. A sponge dipped in a platinum solution is held against the rotating tantalum core. The process is continued until the desired thickness of platinum is formed on the surface of the tantalum.

In the platinizing and heat treatment process according to the present invention, a platinum black powder coating is deposited on the tantalum workpiece by electrolysis. The coated workpiece is then placed in a furnace which is heated to about 1050° to 1150° C. This heat treatment results in the diffusion of the platinum into the surface of the tantalum. This diffusion of the platinum into the surface of the tantalum results in a tantalum part containing a platinum surface which is electrically and mechanically superior to plated platinum parts. The process of the present invention results in a stable platinum layer on the tantalum surface and makes the electrode abrasion resistant. Further, the platinum layer made according to the present invention is thinner than conventionally plated platinum layers.

In a preferred embodiment of the present invention a tantalum workpiece, suitable for ultimate use as an electrode in the detection of faults in a reaction vessel, is sandblasted to render the surface clean and free of dirt and grease. The tantalum core is in the form of a one piece 5/8 inch flat head screw and comprises 90% by weight tantalum and 10% by weight tungsten. The core is then brushed off and cleaned with a 20% HCl solution and washed. The core may be stored in distilled water if platinizing is to be done at a later stage.

The following materials and apparatus were used in the platinizing process:

1. Beaker (200 ml)
2. Platinizing Solution (150 ml)
3. Six volt DC power source
4. Small strip of platinum metal ($1\frac{1}{2} \times 1\frac{1}{4} \times 1/32$ inches)

The platinizing solution is prepared in the beaker. The solution contains 3 gms of chloroplatinic acid, 0.02 gms of lead acetate per 100 ml of distilled water. The tantalum core described above is connected to the negative lead of the 6 V DC power supply and the platinum strip is connected to the positive lead of the 6 V DC power supply. Both the platinum strip and the tantalum core are suspended in the solution in the beaker. Only the area of the tantalum that is to be platinized is immersed in the solution. The voltage is then applied for six minutes during which time the platinum black is deposited on the tantalum core. The tantalum electrode is then carefully removed from the solution and rinsed with distilled water. The platinum black deposited is dull black and non-adherent at this stage. The electrode is then placed in a rack and placed in a furnace maintained at a vacuum of about $10^{-6}$ mm of mercury and a temperature of about 1150° C. for $\frac{1}{2}$ hour. This heat treatment results in the platinum being diffused into the surface of the tantalum which exhibits a dull gray appearance. Optionally, the tantalum core may be platinized and heat treated for a second time in order to form a more stable and adherent platinum layer.

It has also been found that the quality of the platinizing and heat treated electrode is better when finer sand is used for blasting, rather than coarser. The surface roughness of the tantalum core after sandblasting was measured by ENGIS roughness meter type 6102E (Engis Equipment Co., Morton Grove, Illinois) and found to be 30–38 micro inches. The surface roughness of the completed platinized and heat treated electrode was measured as 24–28 micro inches.

The addition of lead acetate or other appropriate lead salt to the platinizing solution promotes the adherence of platinum to the tantalum electrode, and is essential for adherence of platinum black to the tantalum surface. Without the presence of a lead salt in the platinizing solution, the deposited platinum black flakes off the surface of the tantalum. Various voltages from about 3–24 volts and varied time periods from about $\frac{1}{2}$ to 6 minutes were found to be satisfactory for the platinizing processes. Six volts for six minutes was found to be optimum from the viewpoint of cost and efficiency, but is not critical for the process. Higher voltages cause excessive platinum deposit on the electrode and lower voltages take longer times to form a platinum deposit on the electrode.

For good quality electrodes it is essential during the heat treatment step to maintain the furnace temperature in the range of about 1050° to 1150° C. for times ranging from about 30 minutes to 1 hour. It was found that below 1050° C. the platinum black does not completely adhere to the tantalum electrode as characterized by a drop in their electrical sensitivity and at temperatures higher than about 1150° C. the electrical sensitivity also drops off and the platinum black sometimes burns off. The furnace is maintained at a vacuum of $10^{-6}$ mm of mercury to prevent oxidation of platinum or tantalum, but vacuums outside this range are also satisfactory. If desired an inert atmosphere could also be used during the heat treating step.

Superior quality of the platinized and heat treated electrode over platinum plated electrodes is further confirmed by the following test, based on the galvanic cell principle. An electrode formed by the above described process and constituting the positive lead is attached to one end of a 0–1 mA ammeter and a piece of tantalum constituting the negative lead is attached to the other end of said ammeter. The electrode and tantalum are placed in a beaker containing 1% HCl water solution and the reading on the ammeter is noted. This reading is known as a no fault reading. The electrode and tantalum are allowed to remain in place for one week. After the one week period a piece of iron is connected to the tantalum and introduced into the HCl solution. This simulates the fault situation when the glass lining of the vessel is damaged and the contents are exposed to the metal. A reading is taken which indicates higher current flow. In the simulated fault situation, the tests have consistently shown higher current readings for platinized and heat treated tantalum electrodes than for platinum plated electrodes. The higher readings signify higher sensitivity of the platinized and heat treated electrodes to the plated electrodes. One such example showed the readings as follows:

| Electrode | No Fault Current mA | Fault Current-mA | |
|---|---|---|---|
| | | After one week initial | After one week 10 min. |
| Conventional Platinum Plated Ta | 0.00 | 1.89 | 1.29 |
| Platinized and Heat Treated Ta | 0.00 | 5.46 | 3.21 |

Thus, it should be appreciated that the present invention of platinizing and heat treating tantalum produces electrodes which measure a fault in a glass lined vessel on a continued basis far more precisely than conventional platinum plated electrodes, even though the plated platinum coating is thicker than the platinized and heat treated platinum layer. Further, the superior performance of the platinized and heat treated platinum layer is achieved at a much lower cost than that of the platinum plating.

Although particular embodiments of the present invention have been disclosed herein for purposes of explanation, further modifications or variations thereof will be apparent to those skilled in the art to which this invention pertains.

What is claimed is:
1. A method which comprises:
   (a) forming a layer of platinum black by electrolysis on the surface of a tantalum or tantalum base alloy electrode;
   (b) heating said electrode in an inert atmosphere at a temperature in the range of about 1050° to 1150° C. for about 30 minutes to 60 minutes, and
   (c) utilizing said electrode for the detection of faults in the glass lining of an iron or steel vessel by disposing said electrode in a conductive medium within said vessel, and measuring the current flow between said electrode and the exposed iron or steel surface at a damage area of the glass lining, whereby the composite electrode and exposed iron or steel form a Pt-Fe cell.

2. The method of claim 1 in which the electrode comprises a tantalum base alloy.

3. The method of claim 2 in which the tantalum base alloy contains tungsten.

4. The method of claim 1 in which the electrode in step (b) is heated under vacuum conditions.